United States Patent [19]
Jones

[11] 3,933,818
[45] Jan. 20, 1976

[54] HETEROCYCLIC COMPOUNDS
[75] Inventor: Geraint Jones, Macclesfield, England
[73] Assignee: Imperial Chemical Industries Limited, London, England
[22] Filed: Aug. 6, 1974
[21] Appl. No.: 495,217

[30]  Foreign Application Priority Data
Sept. 7, 1973  United Kingdom............... 42173/73

[52] U.S. Cl........... 260/250 C; 260/242; 260/319.1; 260/326.16; 424/250
[51] Int. Cl.$^2$..................................... C07D 237/28
[58] Field of Search........................ 260/250 C, 242

[56]  References Cited
UNITED STATES PATENTS
3,669,965  6/1972  White............................. 260/250 C OTHER PUBLICATIONS
Ames et al., J. Chem. Soc., London, 1965, 6036.
Ames et al., J. Chem. So. London(c), 1971, 3088.
Ellis et al., J. Chem. Soc., London(B) 1967, 1285.

*Primary Examiner*—Richard J. Gallagher
*Assistant Examiner*—Mark L. Berch
*Attorney, Agent, or Firm*—Cushman, Darby & Cushman

[57]  ABSTRACT

Optionally substituted 4-oxo-1,4-dihydrocinnolin-3-ylpropionic acid derivatives, processes for their preparation, pharmaceutical compositions containing them, and a method of treatment using them. A representative compound is ethyl 6-ethyl-1-methyl-4-oxo-1,4-dihydrocinnolin-3-ylpropionate. Compounds active as inhibitors of effects following the combination of reagin-like antibodies and their antigens.

5 Claims, No Drawings

HETEROCYCLIC COMPOUNDS

This invention relates to heterocyclic compounds, and more particularly it relates to new cinnoline derivatives which are active as inhibitors of the effects following the combination of reagin-like antibodies and their antigens.

According to the invention there are provided cinnoline derivatives of the formula:

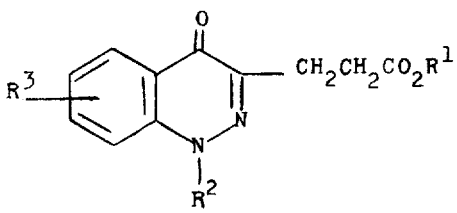

wherein $R^1$ stands for hydrogen or a $C_{1-6}$-alkyl radical, $R^2$ stands for hydrogen or a $C_{1-5}$-alkyl, $C_{3-5}$-alkenyl or benzyl radical, and $R^3$ stands for hydrogen or a methylenedioxy, $C_{1-5}$-alkyl, $C_{1-5}$-alkoxy, phenyl or benzyloxy radical, and non-toxic pharmaceutically-acceptable salts thereof.

Suitable values for $R^1$ are, for example, hydrogen or a methyl, ethyl or isopropyl radical. Suitable values for $R^2$ are, for example, hydrogen or a methyl, ethyl, allyl or benzyl radical. Suitable optional substituents ($R^3$) include, for example, a methylenedioxy, methyl, ethyl, n-propyl, isopropyl, methoxy, isopropoxy, phenyl or benzyloxy radical.

Suitable salts of the invention in the case where the compound of the formula I is sufficiently basic are acid-addition salts derived from inorganic or organic acids which afford non-toxic pharmaceutically-acceptable anions, for example hydrochlorides. Suitable salts in the case where the compound of the formula I is sufficiently acidic are salts in which the said compound provides the anion and the cation is non-toxic and pharmaceutically-acceptable. Examples of such salts are ammonium, alkali metal, alkaline earth metal or aluminium salts, or salts with non-toxic pharmaceutically acceptable organic bases, for example triethanolamine or ethylenediamine.

Preferred compounds of the invention are ethyl 6-ethyl-1-methyl-4-oxo-1,4-dihydrocinnolin-3-ylpropionate, 6-ethyl-4-oxo-1,4-dihydrocinnolin-3-ylpropionic acid and its ethyl ester, and 6-n-propyl-4-oxo-1,4-dihydrocinnolin-3-ylpropionic acid.

According to a further feature of the invention there is provided a process for the manufacture of those of the compounds of the formula I wherein $R^1$ and $R^2$ stand for hydrogen and $R^3$ has the meaning stated above, and non-toxic pharmaceutically-acceptable salts thereof, which comprises reacting a benzazocine derivative of the formula:

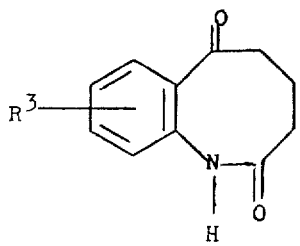

wherein $R^3$ has the meaning stated above, with an alkyl nitrite and an inorganic acid in the presence of a small amount of water.

A suitable alkyl nitrite is, for example, n-butyl nitrite. A suitable acid is, for example, hydrochloric or sulphuric acid. The reaction is conveniently carried out in an inert organic solvent, for example an ether, for example 1,2-dimethoxyethane. The amount of water used in the reaction mixture is not critical; we have found that approximately 0.5-0.6% by volume gives satisfactory results.

Many of the said benzazocine derivatives are new compounds and they may be obtained by the following reactions:

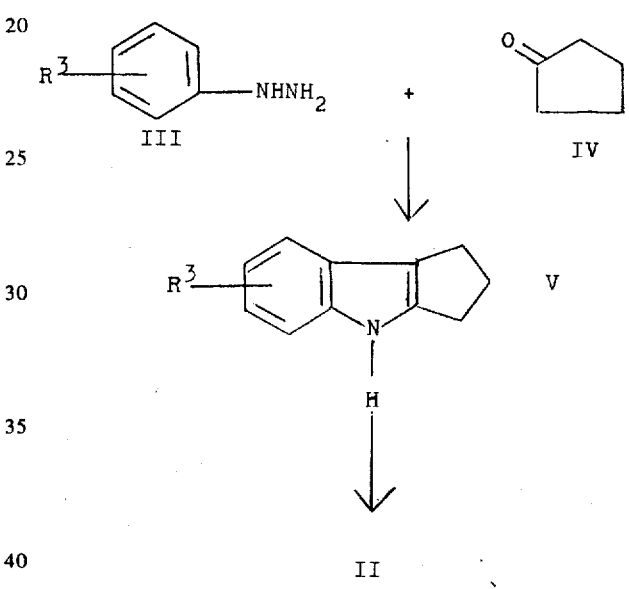

The phenylhydrazine derivatives (III), wherein $R^3$ has the meaning stated above, may be obtained by standard synthetic procedures. Heating one of these compounds with cyclopentanone (IV) in the presence of dilute sulphuric acid, or heating the hydrochloride of one of these phenylhydrazine derivatives with cyclopentanone, affords the corresponding indole derivative of the formula V. Treatment of the latter compound at room temperature with sodium periodate in a mixture of methanol and water, together with tetrahydrofuran if there are solubility problems, affords the product of the formula II.

According to a further feature of the invention there is provided a process for the manufacture of the esters of the formula I wherein $R^1$ stands for a $C_{1-6}$-alkyl radical, $R^2$ stands for hydrogen, and $R^3$ has the meaning stated above, and non-toxic pharmaceutically-acceptable salts thereof, which comprises esterifying the corresponding carboxylic acid wherein $R^1$ stands for hydrogen, or a corresponding acid halide or anhydride.

Any of the standard esterification procedures may be used, for example reacting the carboxylic acid with a $C_{1-6}$-alkanol in the presence of hydrogen chloride at about 50° to 150°C., for example under reflux.

According to a further feature of the invention there is provided a process for the manufacture of those of the compounds of the formula I wherein $R^1$ stands for a $C_{1-6}$-alkyl radical, $R^2$ stands for a $C_{1-5}$-alkyl, $C_{3-5}$-alkenyl or benzyl radical, and $R^3$ has the meaning stated above, and non-toxic pharmaceutically-acceptable salts thereof, which comprises reacting an alkali metal derivative of the formula:

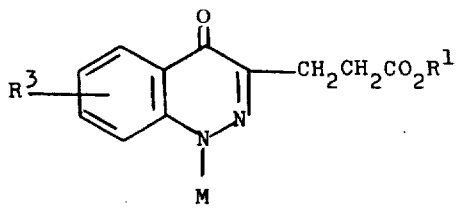

VI wherein $R^1$ and $R^3$ have the meanings stated immediately above and M stands for a sodium or potassium atom, with a halide reactant of the formula $R^2Hal$, wherein $R^2$ has the meaning stated immediately above and Hal stands for a chlorine, bromine or iodine atom.

As a suitable halide reactant there may be mentioned, for example, methyl iodide, ethyl bromide, allyl bromide or benzyl chloride. The reaction is conveniently carried out in an organic solvent, for example dimethylformamide, at room temperature or at a moderately elevated temperature, for example 60°–70°C. The alkali metal derivatives used as starting material may be obtained by reacting the corresponding compound wherein $R^2$ stands for hydrogen with the hydride or amide of sodium or potassium, in a dry inert solvent, for example dimethylformamide, at room temperature.

The compounds of the formula I wherein $R^1$ stands for hydrogen and $R^2$ and $R^3$ have the meaning stated above, and non-toxic pharmaceutically acceptable salts thereof, may be obtained by hydrolysing a compound of the formula:

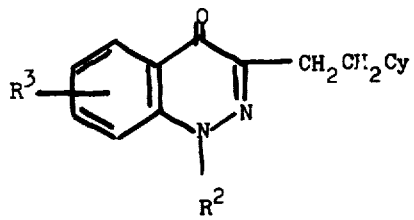

VII wherein $R^2$ and $R^3$ have the meanings stated above and Cy stands for an alkoxycarbonyl, phenylalkoxycarbonyl, phenoxycarbonyl, cyano, carbamoyl ($-CONH_2$) or thiocarbamoyl ($-CSNH_2$) radical.

The hydrolysis is carried out in the presence of water. An organic solvent, for example dioxan or ethanol, may optionally also be present. A suitable hydrolytic agent is, for example, an alkali metal hydroxide, for example sodium hydroxide, or an inorganic acid, for example hydrochloric or sulphuric acid.

The esters of the formula VII may be obtained as described above, and the other starting materials of the formula VII may be obtained by the adaptation of known synthetic procedures.

The salts of this invention may be obtained by means of standard salt-making procedures.

The above-mentioned activity of the compounds of this invention has been demonstrated by their ability to inhibit, in the rat, passive cutaneous anaphylaxis induced by reaginic antibodies to egg albumin, using B.pertussis as an adjuvant. This is a known pharmacological test. The activity of individual compounds of this invention in the test depends upon their precise chemical structure, but generally speaking the compounds show activity in the test at a dose in the region 1–20mg./kg. No toxic effects or undesirable side effects have been observed with the compounds at doses at which they are active in the said test.

When a compound of the invention is used in a warm-blooded mammal, for example man, for the treatment of a disease or syndrome which is initiated by an antigen-antibody reaction, for example allergic asthma, hay fever, urticaria or an auto-immune disease, it is recommended that said compound be administered orally or by inhalation at a dose of 0.01mg./kg. to 1mg./kg. at appropriate intervals, for example at 6-hourly intervals during the day. Alternatively, the said compound may be administered intravenously at a total daily dose of about 70mg. per man.

According to a further feature of the invention there are provided pharmaceutical compositions comprising a compound of the formula I, wherein $R^1$, $R^2$ and $R^3$ have the meanings stated above, or a non-toxic pharmaceutically acceptable salt thereof, and a pharmaceutically-acceptable diluent or carrier.

The pharmaceutical compositions of the invention are obtainable by well known methods using conventional diluents or carriers. The compositions may be in a form suitable for administration by inhalation. Suitable compositions comprise a mixture of the active ingredient with a solid diluent or carrier, for example lactose, the said mixture being in fine particulate form suitable for administration from a powder inhalation device. Alternatively, the compositions may be administered by inhalation in the form of a suspension or solution in a suitable liquid, for example water or an aqueous or non-aqueous medium, using a conventional nebulizer or a pressurised container. Alternatively, the pharmaceutical compositions of the invention may be orally-administrable or injectable formulations, for example compositions suitable for oral or intravenous administration, for example tablets, capsules or sterile aqueous solutions or suspensions.

The pharmaceutical compositions of the invention may contain, in addition to a compound of formula I or a non-toxic pharmaceutically-acceptable salt thereof, one or more known active ingredients selected from β-adrenergic stimulants, for example isoprenaline, adrenaline, orciprenaline or isoethacine, or a pharmaceutically-acceptable acid-addition salt thereof, for example a sulphate, and prostaglandins having bronchodilatory activity, for example prostaglandin $E_1$ or $E_2$, and phosphodiesterase inhibitors selected from the following compounds:- a. 3-acetamido-6-methyl-8-n-propyl-s-triazolo[4,3-a]-pyrazine;

b. 2-amino-4,6-di-$C_{1-4}$-alkyl-5-oxo-4,5-dihydro-s-triazolo-[1,5-a]pyrimidines, for example 2-amino-6-methyl-5-oxo-4-n-propyl-4,5-dihydro-s-triazolo[1,5-a]pyrimidine;

c. theophylline and related 3,5-di-$C_{1-4}$-alkyl-xanthines; and d. 6,8-di-$C_{1-4}$-alkyl-5,6-dihydro-5-oxo-s-triazolo[4,3-c]-pyrimidines, for example 5,6-dihydro-5-oxo-6,8-di-n-propyl-s-triazolo[4,3-c]pyrimidine.

The pharmaceutical compositions of the invention may contain from 1% to 50% by weight of a compound of formula I or a non-toxic pharmaceutically-acceptable salt thereof.

The invention is illustrated by the following Examples:

EXAMPLE 1

A suspension of 4,5-dihydro-1H,3H-1-benzazocine-2,6-dione (1g.) in 1,2-dimethoxyethane (20ml.) and water (0.1ml.) was prepared, and freshly-prepared n-butyl nitrite (0.84g.) was added. Hydrogen chloride gas was bubbled through the mixture at 25°C. for 5 minutes, and the resulting solution was stirred overnight at room temperature. The solution was then diluted with water (10ml.), the mixture warmed for 5 minutes on a steam bath, and the resulting mixture filtered. The solid residue was crystallised from aqueous ethanol, and there was thus obtained 4-oxo-1,4-dihydrocinnolin-3-ylpropionic acid, m.p. 226°-8°C.

In a similar manner, using the appropriate substituted benzazocine derivative as starting material, the following compounds were obtained:

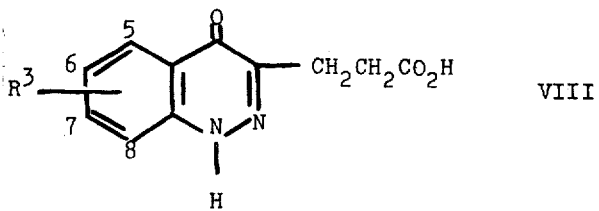

VIII

| $R^3$ | Crystallisation solvent | m.p. (°C.) |
|---|---|---|
| 6-Et | aqueous ethanol | 240–1 |
| 6-n-Pr | aqueous acetic acid | 230–1 |
| 6-iso-Pr | product not crystallised, but isolated by acidification of sodium salt with concentrated hydrochloric acid. | 228–30 |
| 6-PhCH$_2$O | ethanol | 245–7 |
| 6-MeO | aqueous ethanol | 256–8 |
| 6-iso-PrO | aqueous acetic acid | 210–3 |
| 6-Ph | aqueous acetic acid | 306–10(dec.) |

The 8-ethyl-4,5-dihydro-1H,3H-1-benzazocine-2,6-dione used as starting material for the preparation of the above-mentioned 6-ethyl derivative was obtained as follows:

a. To a suspension of 4-ethylaniline (90g.) in water (280ml.) was added concentrated hydrochloric acid (38% w/w, 280ml.), and the mixture was warmed on a steam bath. The suspension obtained was stirred and cooled to 0°C., and a solution of sodium nitrite (52.1g.) in water (180ml.) was added during 45 minutes, the temperature being maintained at −10° to −5°C. by cooling. The dark solution was stirred at 0° C. for a further 30 minutes, and then filtered through celite. The filtered diazonium salt solution (stored at 0°C.) was added in portions to a stirred fresh mixture of sodium dithionite (500g.) in ice-cold water 1 l.) keeping the temperature at 5°–10°C. After the addition of each batch of the diazonium salt solution, further dithionite (total 500g.) was added in portions. After the addition was complete (45 minutes), the mixture was stirred at room temperature overnight. The mixture was separated by filtration and the filtered solid was suspended in water (1 l.), basified with sodium hydroxide solution, and the mixture extracted with ethyl acetate (3 × 250ml.). The combined extracts were washed with a minimum of water, dried (MgSO$_4$), and evaporated to give 4-ethylphenylhydrazine as a low melting solid.

b. The above hydrazine derivative (80g.) and cyclopentanone (50g.) were mixed and heated on a steam bath for 15 minutes. A solution of concentrated sulphuric acid (40ml.) in water (720ml.) was added and the mixture was heated for a further 30 minutes. After cooling in an ice-bath, the black solid which separated was filtered off. A solution of the solid in toluene (750ml.) was dried (MgSO$_4$) and filtered, and the filtrate was concentrated. The residue was applied to a silica gel column (1,000g.). Elution with toluene and concentration of the eluate gave 7-ethyl-1,2,3,4-tetrahydrocyclopentan[b]indole, m.p. 74°–9°C.

c. A solution of the above-mentioned indole derivative (50g.) in methanol (1360ml.) was added to a solution of sodium periodate (126g.) in water (728ml.) at room temperature. The solution became warm, and sodium iodate appeared as white needles. After 2 hours the mixture was diluted with water (500ml.) and extracted with methylene dichloride (4 × 150ml.). The combined extracts were washed with water (2 × 100ml.), dried (MgSO$_4$), filtered, and evaporated to dryness. Crystallisation of the residue from toluene (including treatment with charcoal) gave 8-ethyl-4,5-dihydro-1H,3H-1-benzazocine-2,6-dione, m.p. 138°–40°C.

The 8-benzyloxy-4,5-dihydro-1H,3H-1-benzazocine-2,6-dione used as starting material for the preparation of the above-mentioned 6-benzyloxy-4-oxo-1,4-dihydrocinnolin-3-ylpropionic acid was obtained as follows:

d. A solution of 4-benzyloxyphenylhydrazine hydrochloride (50.2g.) and cyclopentanone (33.6g.) in ethanol (1500ml.) was heated on a steam bath for 5 hours. The hot mixture was filtered and the filtrate evaporated to ca 750ml., whereupon 7-benzyloxy-1,2,3,4-tetrahydrocyclopentan[b]indole, m.p. 110°–2°C., crystallised. Evaporation of the mother liquor to dryness, chromatography of the residue on silica gel (600g.), and elution with toluene, gave a further amount of the product, m.p. 114°C.

e. A solution of the said 7-benzyloxy derivative (17.5g.) in methanol (250ml.) and tetrahydrofuran (100ml.) was added to a solution of sodium periodate (28g.) in water (130ml.) at room temperature. The solution became warm and sodium iodate appeared as white needles. After 2 hours the solution was diluted with water (500ml.) and extracted with methylene chloride (4 × 150ml.). The combined extracts were washed with water (2 × 100ml.), dried (MgSO$_4$), filtered, and evaporated. Crystallisation of the residue from toluene (including treatment with charcoal) gave 8-benzyloxy-4,5-dihydro-1H,3H-1-benzazocine-2,6-dione, m.p. 169°–70°C.

The other benzazocine derivatives used as starting materials were obtained in similar manner. As indicated below, in one case the indole intermediate was obtained by procedure (b) above, and in the other cases by procedure (d) above, while in one case the benzazocine derivative was obtained by procedure (e)

above, and in the other cases by procedure (c) above.

| Substituent in benzene ring | Indole derivative-procedure used | Benzazocine derivative-procedure used |
|---|---|---|
| n-Pr | d | c |
| iso-Pr | d | c |
| MeO | d | c |
| iso-PrO | d | c |
| Ph | b | e |

EXAMPLE 2

A suspension of 6-ethyl-4-oxo-1,4-dihydrocinnolin-3-ylpropionic acid (1g.) in methanol (10ml.) was heated under reflux. Hydrogen chloride gas was bubbled through the mixture under reflux for 30 minutes. The mixture was then heated under reflux overnight. The mixture was cooled and diluted with water (50ml.). The resulting mixture was filtered, and the solid residue was crystallised from methanol. There was thus obtained methyl 6-ethyl-4-oxo-1,4-dihydrocinnolin-3-ylpropionate, m.p. 173°–4°C.

In a similar manner, starting with the appropriate propionic acid, there were obtained the following compounds:

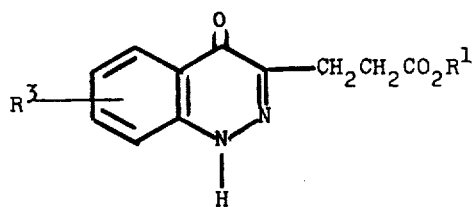

IX

| $R^1$ | $R^3$ | crystallisation solvent | m.p. (°C.) |
|---|---|---|---|
| Et | 6-Et | acetonitrile | 179–80 |
| iso-Pr | 6-Et | acetonitrile | 182–3 |
| Et | 6-n-Pr | acetonitrile | 175–7 |
| Et | 6-iso-Pr | acetonitrile | 155–60 (dec.) |
| Me | 6-iso-Pro | acetonitrile | 205–7 |
| Et | 6-iso-PrO | acetonitrile | 184–6 |
| Et | 6,7-OCH$_2$O | acetonitrile | 231–3 |
| Me | 6-Ph | methanol | 255–7 |
| Et | 6-Ph | ethanol | 202–3 |

Some of the propionic acids used as starting materials were obtained as described in Example 1, and the remainder were obtained by similar procedures.

EXAMPLE 3

Sodium hydride in oil (0.33g.) was washed free from oil with petroleum ether (b.p. 40°–60°C.; 3 × 5ml.) and then suspended in dimethylformamide (10ml.). Ethyl 6-ethyl-4-oxo-1,4-dihydrocinnolin-3-ylpropionate (1g.) was added, and the mixture was stirred at room temperature for 15 minutes. Methyl iodide (0.5ml.) was added, and the mixture was stirred at 60°–70°C. for 2 hours. The mixture was cooled and poured into water (100ml.), and the resulting mixture was filtered. The solid residue was crystallised from petroleum ether (b.p. 60°–80°C.), and there was thus obtained ethyl 6-ethyl-1-methyl-4-oxo-1,4-dihydrocinnolin-3-ylpropionate, m.p. 92°–94°C.

The following compounds were obtained in a similar manner from the appropriate starting materials, except that, when the reaction mixture was poured into water (100ml.), instead of being filtered, the mixture was extracted with diethyl ether (3 × 100ml.), the combined extracts washed with saturated sodium chloride solution (100ml.), dried (MgSO$_4$) and evaporated to dryness. The residue was crystallised using the solvents stated below. In this way, the following compounds were obtained:-

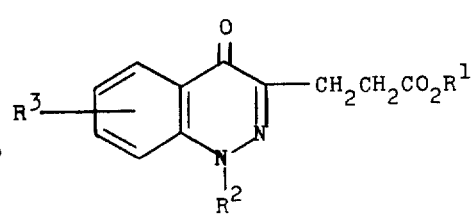

I

| $R^1$ | $R^2$ | $R^3$ | Crystallisation solvent | m.p. (°C.) |
|---|---|---|---|---|
| Et | allyl | 6-Et | pet. ether (b.p. 80–100°C.) | 80–2 |
| Et | Et | 6,7-OCH$_2$O | toluene-pet. ether (b.p. 60–80°C.) | 125–7 |
| Me | Me | 6-Ph | ethyl acetate-pet. ether (b.p. 60–80°C.) | 130–2 |
| Me | Me | 6-iso-Pro | toluene-pet. ether (b.p. 60–80°C.) | 124–6 |
| Et | PhCH$_2$ | 6-Et | pet. ether (b.p. 60–80°C.) | 110–2 |

What we claim is:
1. A cinnoline derivative of the formula:-

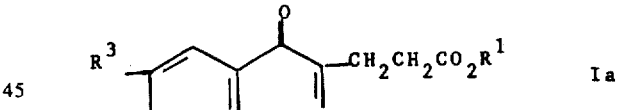

Ia or

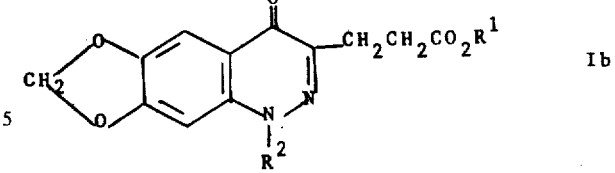

Ib wherein $R^1$ stands for hydrogen or a $C_{1-6}$-alkyl, $R^2$ stands for hydrogen or a $C_{1-5}$-alkyl or $C_{3-5}$-alkenyl, and $R^3$ stands for hydrogen or a $C_{1-5}$-alkyl, $C_{1-5}$-alkoxy, phenyl or benzyloxy, or a non-toxic pharmaceutically-acceptable salt thereof.

2. A compound as claimed in claim 1 wherein $R^1$ stands for hydrogen or a methyl, ethyl or isopropyl radical, $R^2$ stands for hydrogen or a methyl, ethyl, allyl or benzyl radical, and $R^3$ stands for hydrogen or a, methyl, ethyl, n-propyl, isopropyl, methoxy, isopropoxy, phenyl or benzyloxy radical.

3. A salt as claimed in claim 1 in the case where the compound of the formula Ia or Ib is sufficiently basic, which salt is an acid-addition salt derived from an acid which affords a non-toxic pharmaceutically-acceptable anion.

4. A salt as claimed in claim 1 in the case where the compound of the formula Ia or Ib is sufficiently acidic, in which salt the said compound of the formula Ia or Ib provides the anion, and the cation is non-toxic and pharmaceutically-acceptable and selected from the group consisting of ammonium, alkali metal, alkaline earth metal, aluminum ions and organic cations.

5. A compound as claimed in claim 1 which is either ethyl 6-ethyl-1-methyl-4-oxo-1,4-dihydrocinnolin-3-ylpropionate, 6-ethyl-4-oxo-1,4-dihydrocinnolin-3-ylpropionic acid or its ethyl ester, or 6-n-propyl-4-oxo-1,4-dihydrocinnolin-3-ylpropionic acid.

* * * * *